US005374558A

United States Patent [19]

Binns et al.

[11] Patent Number: 5,374,558

[45] Date of Patent: Dec. 20, 1994

[54] FOWLPOX VIRUS PROMOTER

[75] Inventors: Matthew M. Binns; Michael E. G. Boursnell; Joan I. A. Campbell, all of Huntingdon, England

[73] Assignee: British Technology Group Ltd., London, England

[21] Appl. No.: 669,404

[22] PCT Filed: Oct. 20, 1989

[86] PCT No.: PCT/GB89/01257

§ 371 Date: Mar. 20, 1991

§ 102(e) Date: Mar. 20, 1991

[87] PCT Pub. No.: WO90/04638

PCT Pub. Date: May 3, 1990

[30] Foreign Application Priority Data

Oct. 21, 1988 [GB] United Kingdom ................. 8824746

Apr. 21, 1989 [GB] United Kingdom ................. 8909043

[51] Int. Cl.[5] ...................... C12N 15/79; C12N 15/86; C12N 15/11; C12N 15/39

[52] U.S. Cl. ................................ 435/320.1; 536/24.1; 536/23.72; 435/235.1; 935/6; 935/32

[58] Field of Search ................. 435/69.1, 235.1, 320.1, 435/172.3, 240.2; 536/27, 23.72, 24.1; 935/6, 11, 32, 36, 57, 65

[56] References Cited

U.S. PATENT DOCUMENTS 5,093,258 3/1992 Cohen et al. ..................... 435/235.1

5,174,993 12/1992 Paoletti ................................ 424/89

FOREIGN PATENT DOCUMENTS 8903429 4/1989 WIPO .

8903879 5/1989 WIPO .

OTHER PUBLICATIONS

Weir, J. P. et al. 1984, *J. Virol.* vol. 51 pp. 662–669.

Coupar, B. E. H. et al. 1986. Eur. J. Immunol. vol. 16 pp. 1479–1487.

Prideaux, C. T. et al. 1987. Arch. Virol. vol. 96 pp. 185–199.

*Primary Examiner*—Christine M. Nucker

*Assistant Examiner*—Mary E. Mosher

*Attorney, Agent, or Firm*—Nixon & Vanderhye

[57] ABSTRACT

Avipox virus, especially fowlpox virus (FPV), for promoting the transcription of a foreign gene inserted in a fowlpox virus (FPV) vector, said DNA comprising the promoter of the gene which encodes a protein of about 53 amino acids in a sequence beginning:

Met Glu Ser Pro Ala Glu Lys Pro Thr Ile

Asp Ser Pro Pro Glu Gly Asn Val Gln Pro or a variation of such an amino acid sequence, said promoter consisting substantially of sequence to the 5′ end of said gene which is non-coding for said gene.

5 Claims, No Drawings

FOWLPOX VIRUS PROMOTER

BACKGROUND OF THE INVENTION

1. Field of the Invention

The invention is in the field of recombinant DNA technology and relates to an avipox, especially fowlpox, virus promoter useful for the expression of foreign DNA inserted Into a fowlpox virus vector.

2. Description of the Prior Art

Poxviruses are large viruses with a complex morphology containing linear double-stranded DNA genomes. They are among the few groups of DNA viruses that replicate within the cytoplasm of the cell. They are subclassified into six genera: orthopoxviruses, avipoxviruses, capripoxviruses, leporipoxviruses, parapoxviruses and entomopoxviruses. Vaccinia virus (VV), an orthopoxvirus, is the most widely studied of the poxviruses, and is the subject of U.S. Pat. No. 4,603,112 (Paoletti et al.,). Fowlpox virus (FPV) is an avipoxvirus or avian poxvirus.

Recent advances in recombinant DNA technology have allowed VV to be used as a vector to carry and express foreign genes. Foreign DNA Is Introduced Into the VV genome by a process of homologous recombination. Homologous recombination involves essentially (1) pre-selecting a length of the VV genome in some region which does not impair the replication and normal functioning of the virus (hereinafter called a "non-essential region"), (2) making a construct comprising a VV promoter and a length of foreign DNA within a copy of the non-essential region (NER) so that the foreign DNA is under the control of the promoter and so that the promoter-foreign DNA combination is flanked by extensive sequences of non-essential region of VV DNA, (3) co-infecting appropriate tissue culture cells with the VV and with the construct and (4) selecting cells containing VV in which the pre-selected length has been recombined in vivo so that it is replaced in the genome by the construct DNA. The recombinant W expresses the foreign gene in vivo, stimulating the immunity to the protein in an appropriate host. The procedure has considerable potential for use in vaccination.

More recently, similar technology has been applied to fowlpox virus (FPV). Although VV promoters have been used successfully in laboratory constructs of FPV, It is undesirable to incorporate elements of such VV, an orthopoxvirus which has a wide host range recombinant vaccine, for fear of recombination events which could pose a health risk. There is therefore a need to develop FPV promoters for use in recombinant FPV. Certain FPV promoters designated as promoters of the "FP4b" gene have been described in UK Patent Application 8824746, now Publication No. 2211504A, or PCT Application GB 88/00922, now Publication No. W0/89/03879 (NRDC). However, each promoter has its own peculiar characteristics of strength and timing of promotion. A choice of promoters is therefore very highly desirable.

SUMMARY OF THE INVENTION

When the prior applications were filed, both on Oct. 21, 1988, their subject matter was enlarged shortly before filing to include the promoter of another gene known as the "790 bp gene" because it lay within a 790 base pair EcoRI fragment of the strain of FPV under investigation. The two prior applications were our first applications in any country for this particular subject matter. As a result of further work, it is now possible to define the "790 bp gene", and therefore the promoter, more precisely. The present invention provides this promoter and this application claims priority of UKPA 8824746 filed Oct. 21, 1988 and of another application filed on Apr. 21, 1989, before any publication of the promoter occurred in the prior applications (or elsewhere).

The promoter of the invention is defined by reference to the gene ORF 1 identified in the sequence of the 790 bp fragment shown below. Note that this sequence is provided in the other strand to that shown in UKPA 8824746, but is arranged in the same 5′ and 3′ direction. Further, the exact length of the fragment has been determined as 783 bp. Consequently, position 1 in the sequence below Is the complement of position "795" (an arbitrary number) in UKPA 8824746, while position 758 in the sequence shown below is the complement of position "1" (also an arbitrary number) in UKPA 8824746. (The nucleotides numbered 759–783 below were not sequenced in the prior application), Referring to the sequence below it will be seen that three open-reading frames have been identified, ORFs 1 and 2 are completely within the fragment while ORF 3 lies only partly within it. It has been determined that ORF 1 is the gene which is strongly promoted.

```
  1 ATGATGTTCTATGTTAGGTAATTTAGACTATTCTTTTACTTCAATATTTATAATATCTAA

 61 AGTATGGTAATTTATATAAACATTATTACAAAATAACGTACATTAAAAATGAAAAAGAAC

                        [ORF1]  M   E   S   P   A   E   K   P   T   I   D   S
121 CATTAATATTATTGAACCCTAAAGCCATGGAATCTCCAGCTGAAAAACCAACAATCGATT

      P   P   E   G   N   V   Q   P   P   S   T   D   D   K   G   V   N   T   G   P
181 CTCCCCCAGAAGGGAATGTACAACCTCCATCTACCGATGATAAAGGCGTAAATACCGGAC

      K   P   S   D   G   G   C   C   E   P   E   C   P   Y   K   T   Q   D   T   N
241 CTAAACCTTCTGATGGGGGTTGTTGTGAGCCAGAATGTCCTTACAAAACCCAAGATACTA
                                                                *

      K   *
301 ATAAGTAATTAAATTATTATATTCATTTTTATCTATATCGTAAAACATAAAAAATAGATA
    Y   T   I   L   N   N   Y   E   N   K   D   I   D   Y   F   M   F   F   L   Y

361 TGTATTAATATGACGTAATATATGAATATATAATCTATACGATACACAAAATATCAATAG
    T   N   I   H   R   L   I   H   I   Y   L   R   Y   S   V   C   F   I   L   L
```

-continued

```
                                   [ORF3]   M   F   Y   I   S   I   I   I   V   I
421 TATTATAAAATATAACAGTATACCAACCATAATGTTTTATATAAGTATCATCATCGTTAT
      I   I   F   Y   L   L   I   G   V   M  [ORF2]

      L   L   V   I   P   C   N   I   A   K   I   I   S   P   R   V   K   S   K   L
481 ACTTTTGGTAATACCGTGTAATATCGCTAAAATAATATCTCCCCGTGTTAAGAGCAAGTT

      T   E   N   N   I   E   F   R   Y   K   T   Y   M   E   D   V   V   I   Y   R
541 GACTGAAAATAATATCGAGTTTAGGTATAAAACTTATATGGAAGATGTGGTTATATATCG

      T   D   C   N   T   R   L   I   I   G   V   T   N   T   V   Y   V   V   N   T
601 CACGGATTGTAATACCCGACTAATTATAGGAGTAACAAATACTGTATACGTGGTAAATAC

      T   D   K   S   N   I   T   V   D   F   S   P   D   N   V   S   T   Q   S   G
661 AACCGATAAAAGCAATATTACGGTGGACTTTTCACCCGATAATGTATCGACACAATCAGG

      A   N   Y   I   T   F   I   G   G   Y   D   D   K   I   L   V   C   G   T   N
721 CGCTAATTATATTACATTTATAGGTGGATATGATGACAAAATTCTAGTGTGTGGAACGAA

781 TTC
```

The science of promoters of poxvirus DNA is at present poorly understood. It is Known that certain regions to the 5′ or "upstream" end of a gene serve to assist in transcribing genomic DNA into messenger RNA by binding the RNA polymerase involved in the transcription so that the mRNA which contains the start codon of the gene can be transcribed. Such upstream regions are referred to as the "promoter". It is often not possible to say for certain which nucleotides of the upstream sequence are essential and which are inessential for promotion, nor is the minimum or maximum length of the promoter Known with great precision. Although this lack of precision in the whereabouts and length of the promoter might at first sight seem rather unsatisfactory, it is not a problem in practice, since there is normally no harm in including additional DNA beyond the region which serves to transcribe the DNA. Further as described later, it is possible by tedious experiment to determine this region more precisely. In all these circumstances, it is therefore more appropriate to define the promoter by reference to the gene which it precedes, rather than by reference to the sequence of the promoter.

The strongly promoted "790 bp" gene was identified by research into amounts of mRNA likely to be produced when viral DNA is transcribed. The theory is that strong promoters direct the transcription of greater amounts of RNA than weak promoters. In order to avoid the problems of experimentation in vivo, RNA was prepared in vitro in a manner thought likely to emulate in vivo transcription. The RNA thus prepared was hybridised to BamHI and EcoRI restriction fragments of FPV DNA. Strong hybridisation to several fragments was taken to indicate a strongly promoted gene and by this means such a gene which falls at least partly within a 790 bp EcoRI fragment was identified and the fragment partly sequenced.

These five genes can be defined in various ways, always remembering, of course, that there will doubtless be minor differences in their sequence between one strain or type of FPV and another. One convenient, arbitrary,way of defining them is by reference to an appropriate length of the amino acid sequence which they encode. It may reasonably be assumed that the first 20 amino acids, say, would form a unique sequence in FPV.

Accordingly, the avipox virus promoter DNA of the invention, for promoting the transcription of a foreign gene inserted in a FPV vector, is defined as comprising the promoter of the gene which encodes a protein of about 53 amino acids in a sequence beginning:

Met Glu Ser Pro Ala Glu Lys Pro Thr Ile

Asp Ser Pro Pro Glu Gly Asn Val Gln Pro or a variation of such an amino acid sequence, said promoter consisting substantially of sequence to the 5′ end of said gene which is non-coding for said gene.

With regard to possible variations in the 20 amino acids between different FPV strains, probably there would be at least 90% homology over the whole gene, but there may well be less homology over the first 20 amino acids, perhaps up to 3 or 4 differences. It is confidently believed, however, that no one skilled in the field will be in any doubt as to which gene is intended, despite some such aberration in the amino acid sequence.

While the precise length of DNA required for promotion is not known, it is generally reckoned to be up to 100 base pairs from the RNA start site, but this can be as much as 50 base pairs away from the gene start site (the ATG codon). Accordingly a DNA sequence contained within 200 base pairs, usually within 150 and more usually 100 or even 80 bp, to the 5′-end of the ORF1 gene (immediately preceding the start codon) is of particular interest for the purposes of the invention. The DNA sequence of 146 of base pairs is shown above (ORF1 begins at 147) and the remainder can easily be found by extending the sequence along the FPV genome, using the 790 bp fragment as a probe to identify a clone containing the additional sequence required.

As in all DNA inventions, it will be appreciated that some variation of the nucleotides will be possible, i.e. that the promoter sequence will be capable of variation, as can be determined by experiment.

The invention Includes DNA molecules, recombination vectors, cassettes, recombinant cloning vectors, recombinant FPV made by homologous recombination of a parent FPV with an insert DNA, in vitro cultures of animal cells, methods of vaccination etc., all as described or claimed in our UK Patent Application 8824746, mutatis mutandis with respect to the definition of the "790 bp" ORF 1 gene promoter of the present application.

DESCRIPTION OF THE PREFERRED EMBODIMENTS

The promoter of the invention can be obtained from FPV, but variants thereon are expected in other avipox viruses, e.g. in dovepox virus or canarypox virus. An appropriate strain of dovepox virus is described in European Patent Application Publication No. 284416A. For convenience, the invention is hereinafter described with reference to fowlpox virus, but it will be understood that the promoter could be derived from another avipox virus and, if desired, used in a vector of another avipox virus.

The recombination vector of the invention may be defined as comprising a cloning vector containing a non-essential region (NER) sequence of FPV, said NER being interrupted by DNA which consists of or includes (a) promoter DNA of the invention, followed by (b) a foreign gene (i.e. a gene which it is desired to insert into the FPV vector) transcribable by the promoter.

In one particular aspect, the invention includes a recombination vector which comprises in order:

(1) a first homologously recombinable sequence of the fowlpox virus (FPV) genome, (2) a sequence within a first portion of a non-essential region (NER) of the FPV genome, (3) promoter DNA according to the invention, (4) a foreign gene transcribably downstream of the promoter (whereby when the fowlpox virus RNA polymerase binds to the promoter it will transcribe the foreign gene into mRNA) and (5) a sequence within a second portion of the same NER of the FPV genome, the first and second sequences preferably being in the same relative orientation as are the first and second portions of the NER within the FPV genome, and (6) a second homologously recombinable sequence of the FPV genome, said sequences (1) and (6) flanking the NER in the FPV genome and being in the same relative orientation in the recombination vector as they are within the FPV genome.

In another aspect, the invention includes a DNA construct which comprises a promoter of the invention transcribably linked to a foreign gene. Such a construct or "cassette" can be inserted in a cloning vector, which can then be used as a recombinant vector useful in preparing a recombination vector of the invention.

The invention further includes hosts harbouring the recombination and recombinant vectors of the invention, especially a bacterial host harbouring a plasmid vector.

The invention is further directed to a recombinant FPV which is the product of homologous recombination of FPV with a recombination vector of the invention containing a foreign gene; the process of homologous recombination; animal cells infected with such a recombinant FPV; a process of in vitro culture of these infected cells; and a method of vaccinating a responsive animal, especially a chicken, which comprises inoculating it with the recombination vector of the invention.

Just how much of the 5'-non-coding sequence is necessary for efficient promotion is not known precisely. However, experiments can be carried out to answer this question, and in fact some have been performed for VV. These are fully described in the above-mentioned UKPA 8824746 on pages 12 and 13, the disclosure of which is herein incorporated by reference.

Since some changes in sequence are permissible without loss of the promotional effect, it will be appreciated that it is necessary that the invention should cover sequences which are variant, by substitution as well as by deletion or addition from the non-coding sequence shown above.

The recombination vector could contain additional sequence to that herein referred to as promoter DNA. Additional sequence could comprise (a) additional sequence added to the 5'-end of the promoter, (b) sequence inserted into the promoter without destroying promoter activity or (c) part of the sequence of the FPV gene (inclusive of the ATG initiation codon and onwards), e.g. up to 100 bp thereof.

In the practice of the invention for poultry, a foreign gene relevant to improving the condition of the poultry would be inserted into the fowlpox virus. Preferably the gene will be one appropriate to an in vivo sub-unit vaccine, for example one or more genes selected from infectious Bronchitis Virus (IBV), Infectious Bursal Disease Virus, Newcastle Disease Virus (NDV), Marek's Disease Virus, infectious Laryngotracheitis Virus and genes encoding antigenic proteins of Eimeria species. Particular genes of interest are the spike genes of IBV and the HN and F genes of NDV as described in PCT Patent Application Publication No. 86/05806 and European Patent Application Publication No. 227414A (both National Research Development Corporation). In order for the foreign gene to be correctly translated in vivo it is necessary for the foreign gene to have its own ATG start codon inserted in the region Just following the promoter.

It is necessary to locate a non-essential region (NER) of the FPV, in which to insert the promoter of the invention and the desired foreign gene. In principle, they could be inserted anywhere in the FPV genome which would not harm the basic functions of the virus, or interfere with the action of the FPV promoter or the foreign gene. Preferably the NER is within the terminal inverted repeat of the FPV genome, as described in UK Patent Application No. 8914306.9 or its PCT equivalent PCT/GB89/00698 both filed on Jun. 22, 1989, the disclosure of which is herein incorporated by reference. Two copies of the foreign gene would then be expected to become inserted in the FPV genome, one towards each end.

The preparation of recombinant and recombination vectors, inoculation of birds and all other methodologies relevant to the invention are as described in the aforesaid UKPA 8824746 and all such disclosure is herein incorporated by reference for the purpose of brevity.

For administration to birds as a vaccine, the recombinant virus can be given to birds by any suitable method such as by aerosol, drinking water, oral, intramuscular injection or inoculation into the wing web. Ingredients such as skimmed milk or glycerol can be used to stabilise the virus. It is preferred to vaccinate chicks 1 day old by aerosol administration. A dose of from $10^2$ to $10^8$ pfu, preferably $10^4$ to $10^6$ pfu, of the recombinant FPV per bird is recommended in general.

While the invention is intended primarily for the treatment of chickens it is potentially of interest in relation to other animals which might safely be infected with FPV. It is even possible that it might be considered safe to infect humans with FPV after appropriate trials have taken place. In that event, the realistic choice of foreign gene would become very wide.

The following Example illustrates the invention.

EXAMPLE

Promoters are signals in the vital DNA which direct transcription of RNA. Strong promoters will therefore direct transcription of greater amounts of RNA than weak promoters. This is used as a way of identifying efficient promoters. If radiolabelled vital RNA is hybridised to restriction fragments of viral DNA, immobilised on a nitrocellulose filter, particular regions of the virus containing strong promoters might be identified. For late RNA this might be expected to be difficult since late RNA transcripts are Known to run well past the end of their genes, possibly into adjacent restriction fragments, hence confusing any attempts at mapping. However for early RNA it should be a useful approach. ('Early' RNA is RNA made before DNA replication and 'late' RNA is made after DNA replication, by definition. RNA made even earlier, i.e. before protein synthesis, can be referred to as 'immediate early RNA'). A convenient method of making radiolabelled RNA of the immediate early class is to use a in vitro system containing purified virus, deoxynucleoside triphosphates, one of which is radioactively labelled, and a suitable buffer. This has been described for vaccinia virus by S. Venkatesan & B. Moss, J. Virology 37, 738–747 (1981) and it is found that the RNA produced in vitro (i.e. In a test tube) in this manner has the same pattern as that made in vivo (i.e. in tissue culture).

Virus Purification

Virus was grown in chick embryo fibroblast (CEF) cells and purified as follows: Forty 75 $cm^2$ flasks of CEFs were infected with $5\times10^6$ pfu/flask of PP9 (a plaque-purified isolate of HP440), HP440 being derived by twice passaging in CEF cells the strain HP 438 described in UKPA 8824746). The flasks were incubated at 37° C. for 5 days. The cells were then shaken off into the medium and then spun down at 7,000 rpm for 15 minutes. The supernatant containing the virus was then centrifuged at 15,000 rpm for 30 minutes at 4° C. The virus pellets were pooled and resuspended in 40 ml phosphate-buffered saline (PBS). This was layered onto a cushion of 10 ml of 35% (w/v) sucrose and centrifuged at 15,000 rpm for 30 minutes. The viral pellet was then resuspended in 1 ml of PBS. This was then layered onto a 20–50% (w/v) sucrose gradient and centrifuged at 15,000 rpm for 30 minutes. The two vital bands were collected, pooled, layered onto two 20–60% metrizamide gradients (about 1 ml per gradient) and centrifuged at 30,000 rpm for 18–20 hours. The viral band was then collected (1 ml per gradient). In vitro synthesis of labelled RNA $10^9$ pfu of purified virus particles from the above procedure were used as follows to produce labelled RNA (by the method of S. Venkatesan & B. Moss, 1981 loc. cit). The virus solution was made to 0.05% Nonidet P-40 (NP-40) and left on ice for 1 hour. This was then added to a solution containing 50 mM Trts-HCl (pH 8.5), 10 mM dithiothreitol, 5 mM ATP, 1 mM each of GTP and CTP, 10 mM $MgCl_2$, 100 μM S-adenosylmethionine (AdoMet), and 100 μCi of $^{32}$P-labelled UTP, the total volume being 5 ml. After 30 minutes at 37° C. fresh AdoMet (the same amount again) was added and the reaction incubated for a further 30 minutes. The reaction was terminated by addition of EDTA to 10 mM, and the tubes were placed on ice. The virus was then pelleted by centrifugation at 30,000 rpm for 30 minutes, the labelled RNA being contained in the supernatant. To the supernatant was added sodium dodecyl sulphate (SDS) to a final concentration of 0.25% and the mixture extracted with an equal volume of phenol saturated in TE (10 mM TRIS-HCl, pH 7.5, 1 mM EDTA). The aqueous layer was removed and extracted with diethyl ether and the RNA precipitated by addition of 1/10 volume of 3M sodium acetate and 2.5 volumes of ethanol. The RNA was spun down at 15,000 rpm for 10 minutes and the pellet resuspended in 4 ml of guanidine thiocyanate solution (6M guanidine thiocyanate, 0.5% sodium N-laurylsarcosine, 5 mM sodium citrate, 0.1M 2-mercaptoethanol). This was layered onto a 1 ml cushion of CsCl/EDTA (5.7M CsCl, O.1M EDTA) and centrifuged at 38,000 rpm for 18–20 hours at 18° C. to pellet the RNA. The supernatant was carefully removed and discarded and the RNA pellet resuspended in 500 μl of diethyl pyrocarbonate-treated water.

Hybridisation to DNA

An EcoRI digest of FPV DNA was separated on 0.9% agarose gels. The DNA was transferred to nitrocellulose filters by Southern blotting. The filters were prehybridised in 10 ml of 5×SSC (SSC is O.15M NaCl, O.015M Sodium-citrate) for 2 hours at 60° C. The suspension of labelled RNA being used as a probe was boiled for 3 minutes before addition to the filters. The probe and filters were incubated, with shaking, at 60° C. for 18–20 hours. The filters were washed in 2×SSC, 0.1% SDS at 42° C. for 30 minutes, then in 0.1×SSC, 0.1% SDS at 25 C for 30 minutes, and thereafter exposed to X-ray film.

The labelled vital RNA was found to hybridise strongly to only two EcoRI fragments in the digest of FPV DNA. One was about 790 bp long and the other was 3830 bp. (Some larger sized bands, particularly in the region of about 6,000 bp, hybridised weakly. The 3830 bp band was subsequently identified as within the 11.2 Kb BamHI fragment referred to in UKPA 8824746). The approx. 790 bp fragment (exact length 783 bp) was sequenced as shown above.

In UKPA 8824746, Example 2, it has been shown for other promoters that strong hybridisation of the gene to labelled RNA correlates well with promoter strength (as determined by transient assay).

Identification Of ORF 1

Having established that the whole 790 bp fragment is strongly hybridised to radiolabelled FPV mRNA, the next step was to identify which of the putative genes represented by the three ORFs is responsible for the strong hybridisation, and therefore strong promotion of mRNA. The following experiments were carried out on ORF3 1–3 and, as controls, complementary sequence.

A series of single stranded M13 clones derived from the ORFs were spotted onto nitrocellulose filters and probed with labelled in vitro RNA as already described for the 11.2 Kb BamHI ORFs in UKPA 8824746. This disclosure is herein incorporated by reference. The clones were as follows:

| ORF | Clone ref. | Nucleotide No. Start | Nucleotide No. Finish | Expected to be hybridised (+ = Yes; − = No) |
|---|---|---|---|---|
| 1. (147–305) | US20 | 186 | 295 | + |
| | US11 | 353 | 155 | − |

-continued

| ORF | Clone ref. | Nucleotide No. Start | Finish | Expected to be hybridised (+ = Yes; − = No) |
|---|---|---|---|---|
| 2. (450–301) | US27 | 444 | 219 | + |
| | US21 | 301 | 464 | − |
| 3. (452–783 +) | US12 | 462 | 563 | + |
| | US14 | 695 | 524 | − |

Only the US20 clone hybridized to the in vitro RNA, thus demonstrating that the transcription of ORF1 on the 0.79 Kb EcoRI fragment is responsible for its lighting up brightly. In view of the above-mentioned correlation between mRNA/DNA hybridisation and promoter activity, it may reasonably be assumed that the ORF 1 promoter is a strong one.

It is claimed:

1. Recombinant DNA comprising the promoter sequence which is located immediately 5' to an open reading frame in the fowlpox virus genome, said open reading frame coding for a protein of about 53 amino acids in a sequence beginning:

Met Glu Ser Pro Ala Glu Lys Pro Thr Ile

Asp Ser Pro Pro Glu Gly Asn Val Gln Pro transcribably linked to a foreign gene.

2. Recombinant DNA comprising a non-essential region sequence of fowlpox virus interrupted by DNA according to claim 1.

3. A recombinant cloning vector comprising DNA according to claim 2 and vector sequence.

4. An isolated DNA consisting essentially of the promoter sequence which is located immediately 5' to an open reading frame in the fowlpox virus genome, said open reading frame coding for a protein of about 53 amino acids in a sequence beginning:

Met Glu Ser Pro Ala Glu Lys Pro Thr Ile

Asp Ser Pro Pro Glu Gly Asn Val Gln Pro.

5. DNA according to claim 4, wherein said promoter sequence is of length of up to 146 nucleotides of the sequence:

(5') ATGATGTTCT ATGTTAGGTA ATTTAGACTA TTCTTTTACT TCAATATTTA

TAATATCTAA AGTATGGTAA TTTATATAAA CATTATTACA AAATAACGTA

CATTAAAAAT GAAAAAGAAC CATTAATATT ATTGAACCCT AAAGCC (3').

* * * * *